United States Patent [19]
Stefanchik

[11] Patent Number: 5,340,360
[45] Date of Patent: Aug. 23, 1994

[54] LIGATING CLIP APPLIER

[75] Inventor: David Stefanchik, Mason, Ohio

[73] Assignee: Ethicon, Inc., Somerville, N.J.

[21] Appl. No.: 96,757

[22] Filed: Jul. 23, 1993

Related U.S. Application Data

[63] Continuation of Ser. No. 847,469, Mar. 6, 1992, abandoned.

[51] Int. Cl.⁵ .................................................. A61B 17/00
[52] U.S. Cl. ........................................ 606/142; 227/901
[58] Field of Search ............... 606/139, 142, 143, 151; 227/901, 902

[56] References Cited

U.S. PATENT DOCUMENTS

| | | |
|---|---|---|
| 4,440,170 | 4/1984 | Golden et al. .................. 606/142 |
| 4,602,631 | 7/1986 | Funatsu ........................... 606/142 |
| 4,858,608 | 8/1989 | McQuilkin ....................... 606/142 |
| 5,049,153 | 9/1991 | Nakao et al. ..................... 606/151 |
| 5,084,057 | 1/1992 | Green et al. ..................... 606/142 |
| 5,100,420 | 3/1992 | Green et al. ..................... 606/143 |
| 5,112,343 | 5/1992 | Thornton ......................... 606/142 |
| 5,122,150 | 6/1992 | Puig ................................. 606/139 |

*Primary Examiner*—Stephen C. Pellegrino
*Assistant Examiner*—Gary Jackson

[57] ABSTRACT

A ligating clip applier mechanism having jaws disposed substantially perpendicular to the longitudinal axis of the mechanism. The jaws provide positive rearward retention of a ligating clip. Clips formed with the mechanism have substantially reduced apex gaps and clip gaps. The mechanism provides three degrees of freedom for manipulating tissue or blood vessels.

38 Claims, 9 Drawing Sheets

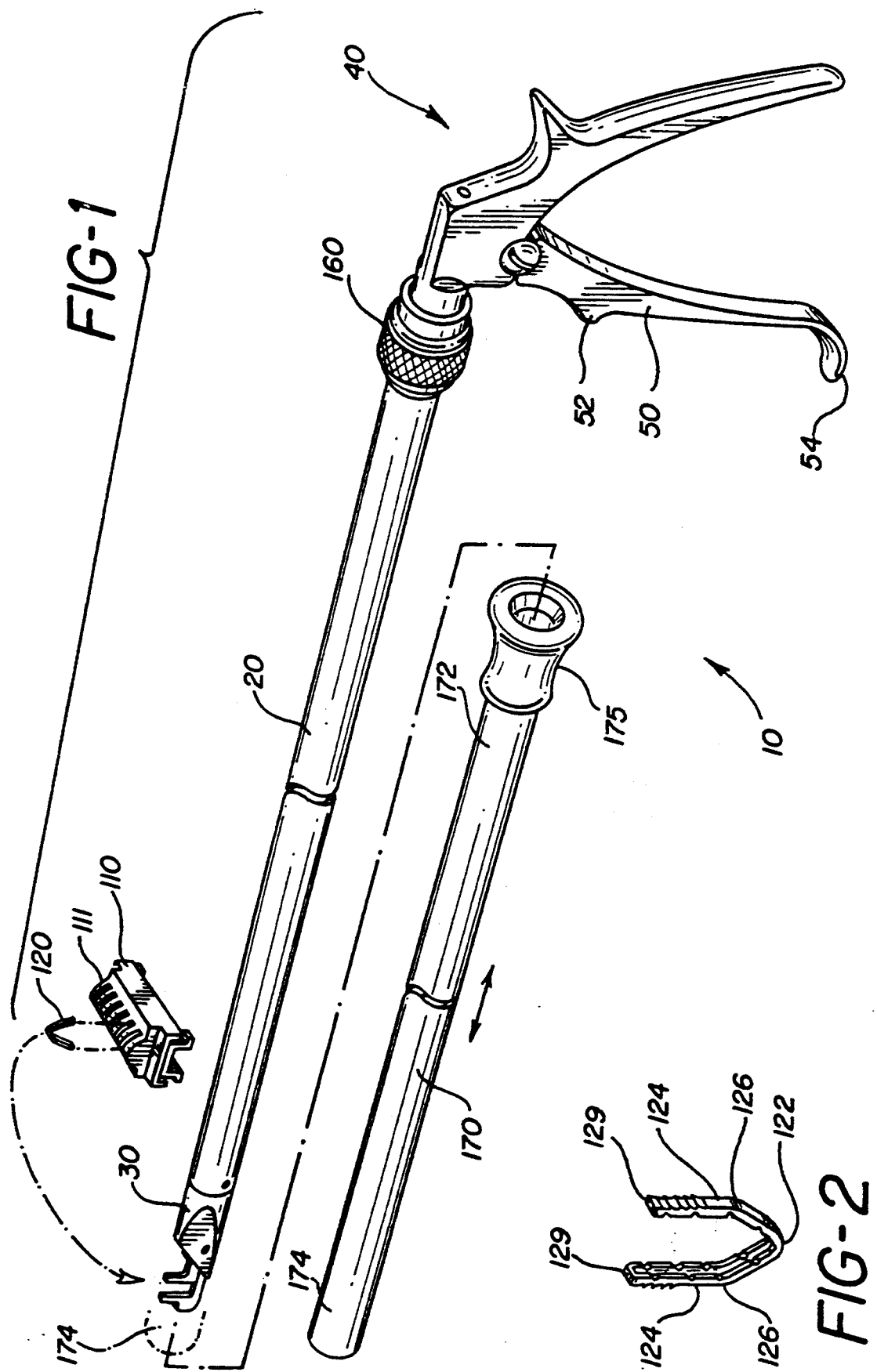

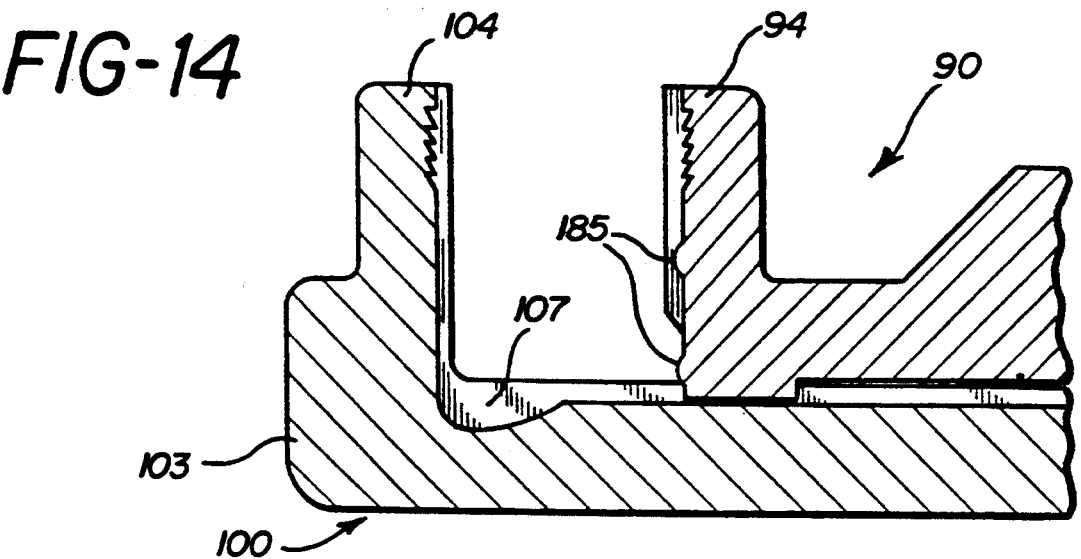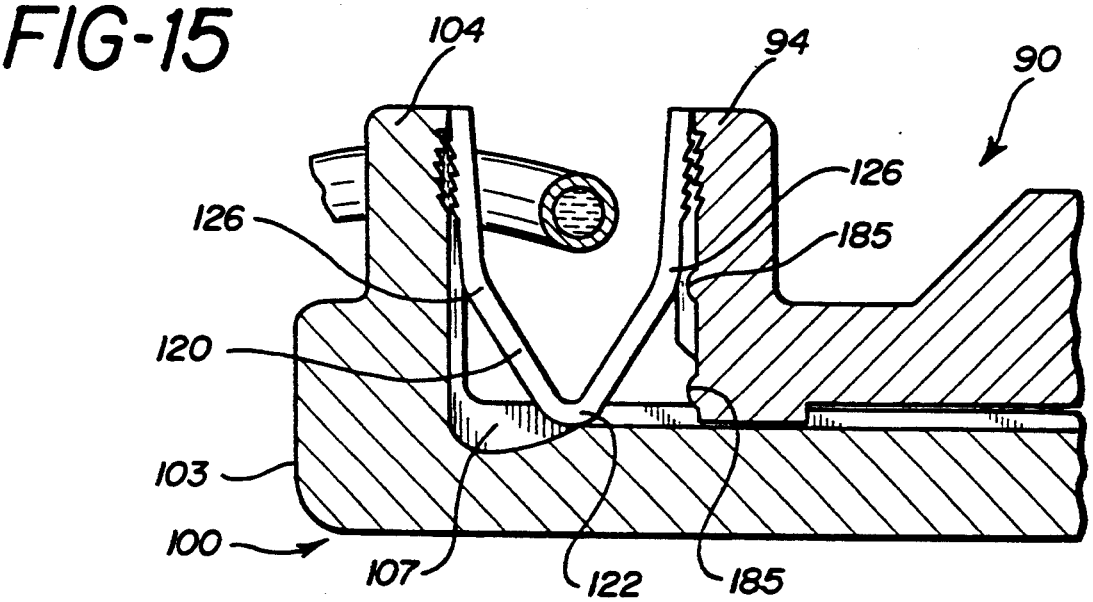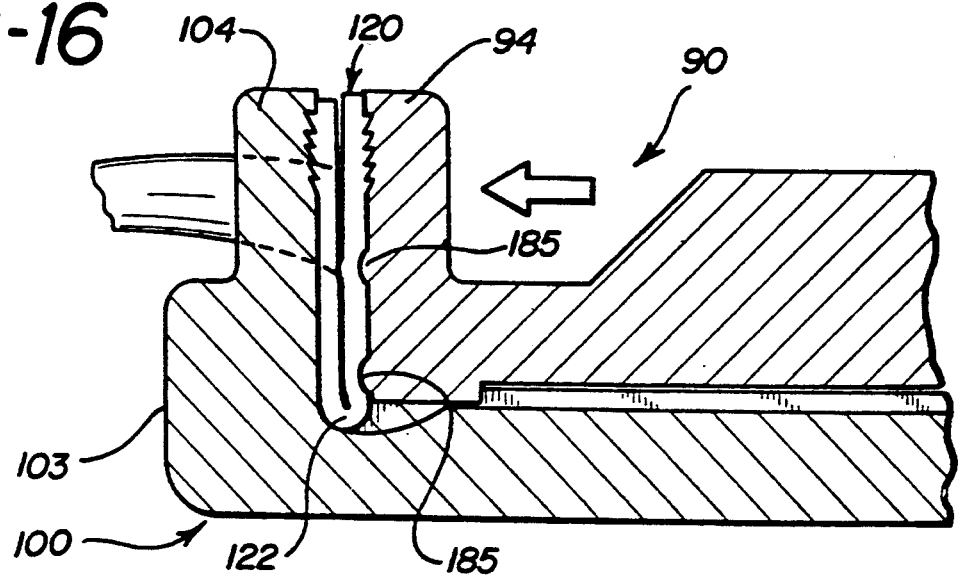

LIGATING CLIP APPLIER

This is a continuation of application Ser. No. 07/847,469, filed Mar. 6, 1992, now abandoned.

TECHNICAL FIELD

The field of art to which this invention relates is surgical instruments, in particular, endoscopic ligating clip appliers.

BACKGROUND OF THE INVENTION

Endoscopic surgical techniques are gaining wide acceptance among both surgeons and patients. There are many benefits associated with the use of endoscopic surgical techniques including reduced avenues for infection, reduced trauma, and a decrease in both the post-operative recuperative period and the duration of the hospital stay. Endoscopic is defined to include laparoscopic and arthroscopic.

Various types of endoscopic surgical instruments have been developed for use in these endoscopic surgical procedures, including ligating clip appliers. Conventional ligating clip appliers currently used in endoscopic procedures typically consist of a frame and a handle having an actuating trigger, an actuating mechanism, and a distal pair of jaws. The jaws typically consist of a pair of opposed jaw members which are angulated with respect to each other. The jaw members typically have inner grooves for retaining the legs of a ligating clip. The outer sides of the jaw members typically have cam surfaces; the jaws are typically closed or actuated by sliding a channel-like member over the cam surfaces thereby forcing the jaw members inward. Ligating clips are inserted between the jaws within the inner grooves, either by an automatic feed or by a single feed. When using a single feed, the jaws are typically inserted into a cartridge containing ligating clips thereby causing a ligating clip to be engaged by the jaws. A conventional ligating clip has a pair of outwardly extending legs connected at an apex. The legs typically extend in a v-shaped manner from the apex and then change direction angularly at a knee to extend outwardly parallel to the longitudinal axis of the clip.

When using a ligating clip applier in an endoscopic procedure, the instrument is initially inserted through a trocar cannula into a body cavity. It will be appreciated that the size of ligating clip is limited, in part, by the inner diameter of the trocar. The clip is then typically applied to a blood vessel or tissue by actuating the trigger which causes the actuating mechanism to engage the jaws, causing the jaws to squeeze the open ligating clip until it forms about the blood vessel or tissue. Typically, at least two clips are applied to a blood vessel or tissue along each side of an intended cut.

There are several deficiencies associated with conventional endoscopic ligating clip appliers currently used in endoscopic surgical procedures. One deficiency relates to the configuration of the jaws of the conventional clip applier. A clip formed by conventional jaws tends to have a relatively thick clip gap consisting of an apex gap and one or more gaps distal to the apex and proximal to the distal ends of the legs. This thick gap is undesirable. Depending upon the size and mechanical characteristics of the blood vessel clipped, it is possible for the blood vessel to move within the formed clip gap, thereby possibly allowing some blood flow through the clipped vessel. It is also possible that the clip may fall off of the blood vessel and into the body cavity.

Another disadvantage of conventional ligating clip appliers is that they typically do not have rearward clip retention. That is, the legs of a ligating clip are substantially retained by retention grooves in the jaws, however, the apex of the clip and the portions of the legs adjacent to the apex and proximal to the knees are not retained. Typically, as a clip is formed by displacing the jaws inwardly, the clip slides proximally in the grooves, since there is no rearward restraint acting upon the apex. If appropriate care is not taken during forming as the clip slides rearward, the vessel's position with respect to the clip may be changed. This can result in the misapplication of a formed clip.

The jaws of a ligating clip applier are typically used by the endoscopic surgeon to manipulate tissue or move blood vessels. This is done by simply engaging the blood vessel or tissue within the open jaws without actuating the jaws. Using a conventional ligating clip applier the surgeon has only 2.5 degrees of movement freedom. That is, the vessel or tissue may be manipulated by the open jaws up and down, left and right, and in. It would be desirable to have a ligating clip applier having jaws which would provide the surgeon with additional degrees of freedom for manipulating tissue.

Another deficiency associated with conventional ligating clip appliers is that it is often difficult for the endoscopic surgeon to control the position of the blood vessel within the jaws of a conventional ligating clip applier. Typically an endoscopic surgical procedure is performed using an endoscope which does not provide the surgeon with three dimensional depth of field. It is often difficult for the endoscopic surgeon to be absolutely certain that the blood vessel is within the jaws of the ligating clip applier prior to applying or forming a clip. If the blood vessel is not entirely within the jaws when the clip is applied, the blood vessel may be only partially contained by the clip and not fully ligated. In addition, the blood vessel may possibly not be within the jaws at all when the surgeon applies the ligating clip, resulting in the formed clip being released to the body cavity. Typically, the clip must then be retrieved from the patient's body cavity.

Yet another deficiency associated with conventional ligating clip appliers is that the size of a clip is limited, in part, by the internal diameter of a trocar through which the ligating clip applier is inserted. This is due, in part, to the configuration of the jaws of a conventional ligating clip applier wherein the clip is retained by the jaws with the outwardly extending jaws substantially in alignment with the longitudinal axis of the clip applier. Therefore, the overall width of the clip is a limiting factor with regard to insertion through a trocar.

What is needed in this field is a ligating clip applier which overcomes these deficiencies and which is easy to use by the endoscopic surgeon and economical to manufacture.

SUMMARY OF THE INVENTION

Therefore it is an object of the present invention to provide a ligating clip applier apparatus having jaws which provide three degrees of freedom for manipulating blood vessels and tissue.

It is another object of the present invention to provide a ligating clip applier apparatus having jaws which are angulated substantially 90 degrees to the longitudinal axis of the apparatus.

It is yet another object of the present invention to provide a ligating clip applier apparatus having jaws angulated at 90 degrees to the longitudinal axis of the apparatus such that when used to form a clip, the gap of the formed clip is substantially reduced.

It is yet another object of the present invention to provide a ligating clip applier apparatus having rearward retention of a ligating clip.

Yet another object of the present invention is to provide a ligating clip applier which can be inserted through a trocar cannula while loaded with a ligating clip, wherein the ligating clip has an open width greater then the maximum width of a clip capable of being inserted by a conventional ligating clip applier through the same trocar.

Accordingly, an endoscopic ligating clip applier mechanism having jaws angulated at 90 degrees to the longitudinal axis of the mechanism is provided. The endoscopic ligating clip applier mechanism comprises an actuating mechanism and an elongated shaft connected to said actuating mechanism. The elongated shaft defines a longitudinal axis. Further, a pair of jaws is connected to said elongated shaft. The jaws are remotely actuated by the actuating mechanism. The jaws are maintained at substantially perpendicular angles to the longitudinal axis. The mechanism has optional rotation means and optional multiple fire clip feed means.

Yet another aspect of the present invention is an endoscopic clip applier mechanism comprising a pair of clip applying jaws. One of the jaws is stationary with respect to the mechanism, and the second of the jaws is slidable with respect to the mechanism. The jaws are mounted to the distal end of an elongate shaft, the shaft defining a longitudinal axis. The second jaw is slidable along the longitudinal axis of said shaft from an open position for receiving a clip to a closed position wherein a clip is formed or closed. The jaws may have optional coining means to coin the apex gap and/or knee gap of a clip. The mechanism also comprises an actuating means attached to the shaft for operating the jaws. The jaws are substantially perpendicular to the longitudinal axis of the shaft. The mechanism has optional rotation means, and may be formed as part of a multiple fire clip applier mechanism.

Another aspect of the invention is a method of using the above-described endoscopic clip applier mechanisms in an endoscopic surgical procedure.

Yet another aspect of the present invention is a method of forming a ligating clip using the above-described endoscopic clip applier mechanisms.

Yet an additional aspect of the present invention is a combination of a trocar cannula, an endoscopic clip applier and an open ligating clip. The trocar has an inner passage, having an inner diameter, therethrough. The endoscopic clip applier is capable of being employed in said cannula passage. The endoscopic clip applier comprises an actuating mechanism, an elongate shaft defining a longitudinal axis, and a pair of jaws connected to said elongate shaft. The open ligating clip has a pair of outwardly extending legs and is contained within said jaws. The distance between the outside of said legs is at least the inner diameter of the trocar cannula.

Other features and advantages of the invention will become more apparent from the following description and accompanying drawings.

BRIEF DESCRIPTION OF DRAWINGS

FIG. 1 is a perspective view of the endoscopic ligating clip applier mechanism of the present invention. Also seen is a clip and a clip cartridge.

FIG. 2 is a perspective view of a conventional ligating clip.

FIG. 14 is a partial cut-away view of a clip applier of the present invention wherein one of jaws has two shaped members.

FIG. 15 illustrates the jaws of FIG. 14 containing a ligating clip with a blood vessel positioned within the ligating clip prior to formation.

FIG. 16 illustrates the clip of FIG. 15 formed about the blood vessel with one shaped member coining the apex of the clip and the other shaped member coining the leg of the clip.

BEST MODE FOR CARRYING OUT THE INVENTION

Figure 3:
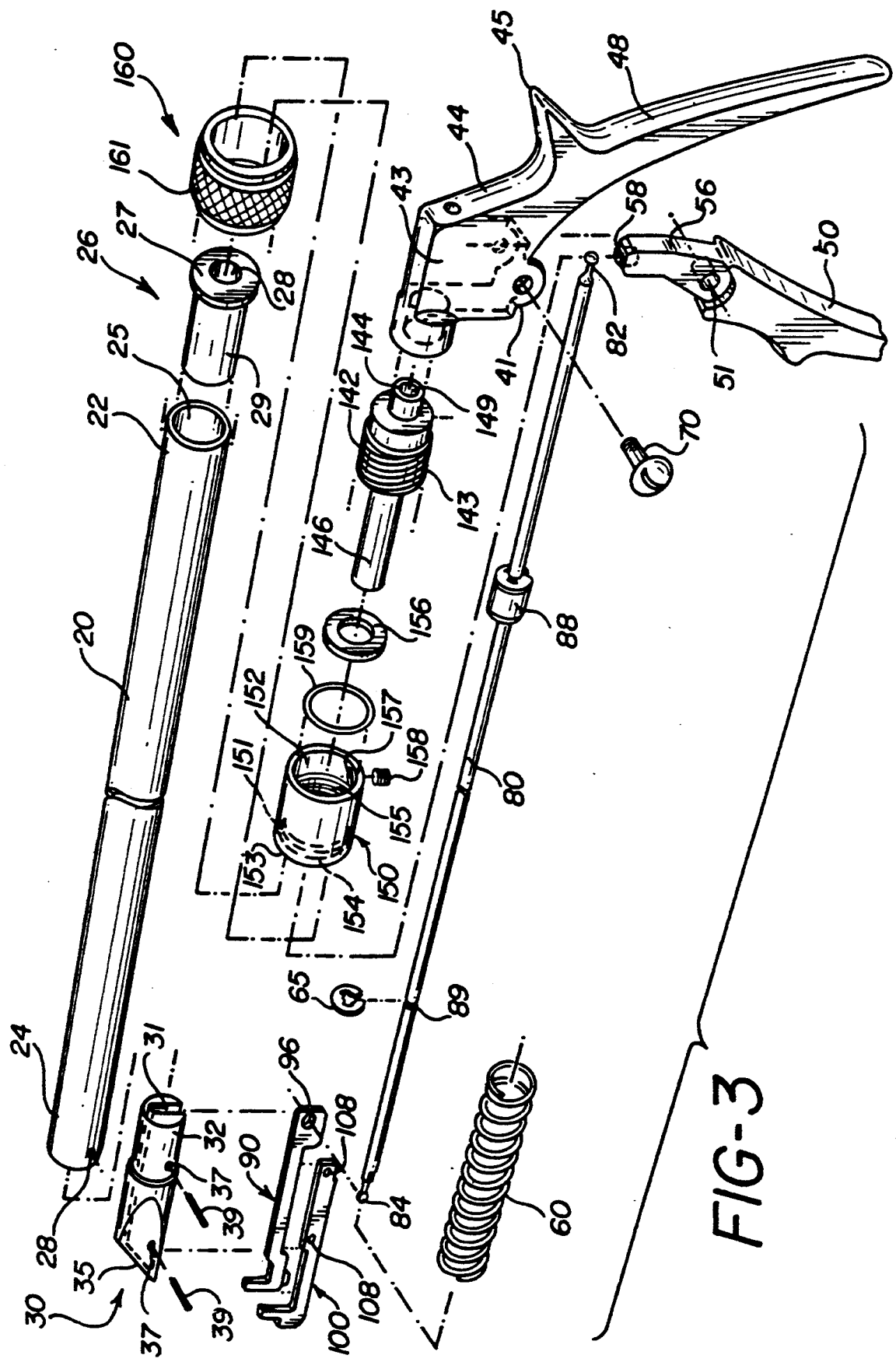
FIG. 3 is an exploded perspective view of the ligating clip applier of the present invention.
Figure 4:
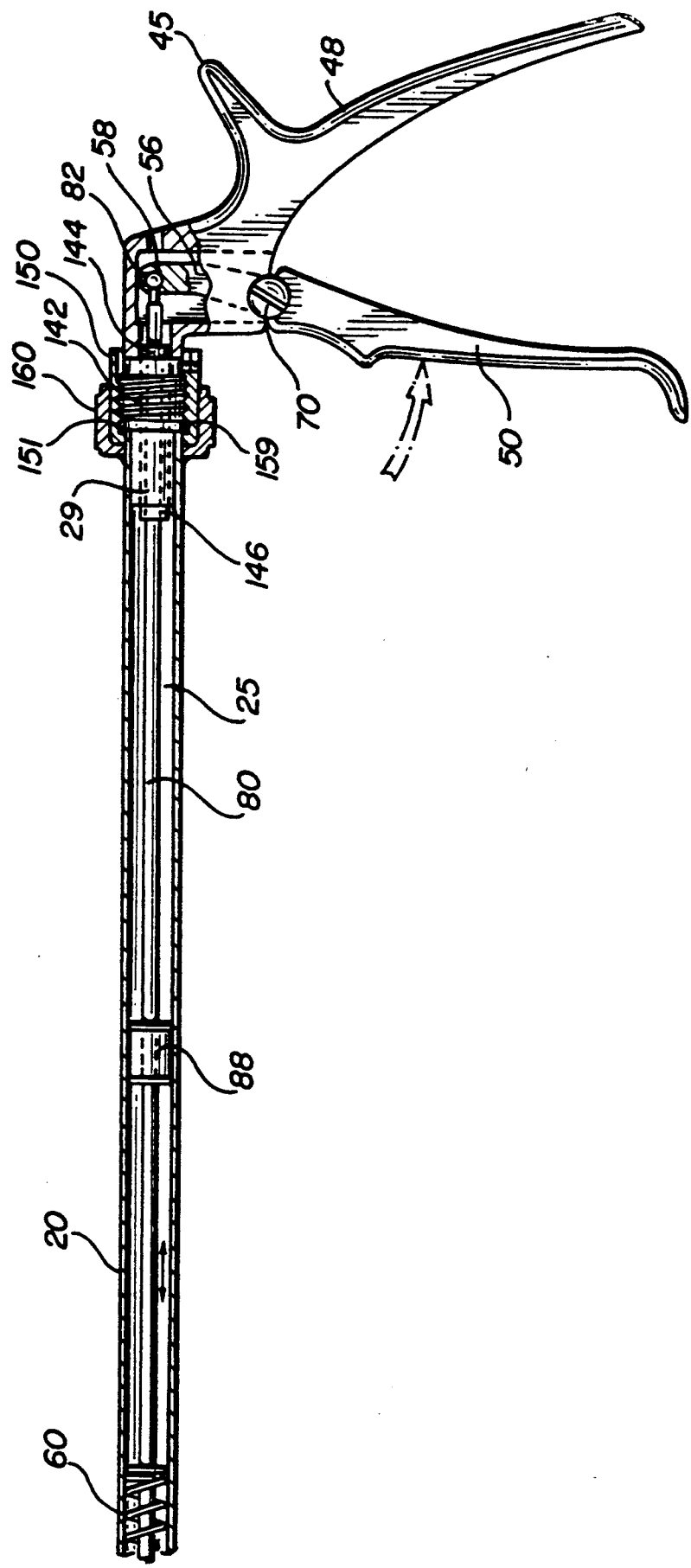
FIG. 4 is a partial cross-sectional view of the endoscopic clip applier mechanism of the present invention proximal to the distal end of the mechanism.

The ligating clip applier mechanism 10 of the present invention is seen in FIG. 1, FIG. 3 and FIG. 4. The ligating clip applier mechanism is seen to have tubular frame 20 having proximal end 22 and distal end 24 as well as longitudinal axis 21. Tubular frame 20 has a passage 25 therethrough for receiving actuating member 80. Attached to the distal end 24 is tubular angulated ferrule 30 having longitudinal rectangular passage 31 therethrough. The ferrule 30 is seen to have proximal tubular end 32 for mounting in the distal end 24 of tubular frame 20 and distal angulated end 35. It can be seen that slot 31 allows ferrule 30 to receive jaws 90 and 100. Ferrule 30 also is seen to have pin mounting holes 37.

Bushing 26, having circular passage 28 therethrough and proximal collar 27, is mounted in the proximal end 22 of tubular frame 20. Specifically, the distal cylindrical section 29 of bushing 26 is engaged, preferably by a force fit, within the proximal end 22 of tubular frame 20. The collar 27 of bushing 26 is positioned external to the proximal end 22 of tubular frame 20.

The tubular frame 20 is rotatably connected to the handle 40 by the connecting coupling 140 which engages both the bushing 26 and the handle 40. The handle 40 is seen to have upper head 44 having internal cavity 43 and downwardly extending handgrip 48. Thumb-grip member 45 projects proximally from handgrip 48. The cylindrical cavity 47 is seen to extend longitudinally from cavity 43 through the distal face of head 44. A pair of semicircular, downwardly extending, opposed mounting tabs 41, having pivot holes 42, are seen for pivotally mounting trigger 50. Actuating trigger 50 is an elongate member which is pivotally mounted to the head 44 of handle 40 between mounting members 41 by pin 70. Trigger 50 also has pivot mounting hole 51 for receiving pin 70. The trigger 50 is seen to have distally protruding finger-grip 52 and curved end 54 which protrudes distally from trigger 40. The trigger has upwardly extending link 56 having end mounting cavity 58 for pivotally engaging the proximal end 82 of elongate actuating member 82. Trigger 50 is mounted to handle 40 by positioning mounting hole 51 between members 41 and inserting pin 70 through pivot holes 42 and mounting hole 51 and securing the pivot pin 70 in a conventional manner.

The connector 140 is seen to be an elongate member having cylindrical body 142, proximal axial shaft 144 and distal axial shaft 146. The connector 140 has an axial passage 149 therethrough for receiving elongate actuating member 80. The outer surface of cylindrical body 142 has screw threads 143. Referring to FIG. 3 and FIG. 4, the proximal shaft 144 is seen to be mounted in cavity 47 of upper head 44 using conventional methods such as welding and the like so that connector 140 is not free to rotate. The distal shaft 144 is mounted in passage 28 of bushing 26 such that bushing 26 and tubular frame 20 are free to rotate together about shaft 144.

Concentrically mounted to connector 140 is the friction adjustor 150. The friction adjustor 150 is a hollow cylindrical member having an open proximal end 152 and an open distal end 153. Distal end 153 has radial inwardly extending flanges 154. The interior wall of friction adjustor 150 has screw threads 155 which mate with screw threads 143 of connector 140. Friction adjustor 150 has threaded hole 157 for receiving set screw 158. Proximal to the interior wall of flange 154 is the annular groove 151 for receiving o-ring 159. The washer 156 is seen to concentrically mounted on shaft 144 prior to mounting the friction adjustor 150 and is contained within the interior cavity of adjustor 150. The proximal face of washer 156 engages the distal side of cylindrical body 142 while the distal face of washer 156 engages the proximal face of collar 27 of bushing 26. Knurled knob 160 is a hollow cylindrical member having proximal opening 162 and distal opening 164 with radial inwardly extending flange 166. Extending axially and distally from the flange 166 is the distal rim 168. The outer surface of knob 160 is seen to have conventional knurling 161. The knob 160 is concentrically mounted over the friction adjustor 150, proximal end 22 of the tubular frame 20 and bushing 26. The distal rim 168 is attached to the proximal end 22 of the tubular frame 20 by conventional methods such as welding so that it is free to rotate about adjustor 150 with tubular frame 20.

As can be seen in FIG. 3 and FIG. 4, the proximal end 22 of support tube 20 along with collar 27 of bushing 27 are mounted within the distal end 153 of friction adjustor 150 distal to o-ring 159. The distal shaft 144 of coupling 140 is mounted within the passage 28 of bushing 26 such that the tubular frame 20 together with the bushing 26 are free to rotate about fixed shaft 144. Tubular frame 20 is constrained axially in the proximal direction by the distal end of cylindrical body 142 and washer 156 which abuts the proximal face of collar 27 of bushing 26. The tubular frame 20 is constrained axially in the distal direction by the proximal face of flange 154 and o-ring 159 which abut the distal side of the collar 27. Tightening friction adjustor 150 with respect to cylindrical member 142 of coupling 40, by rotating the friction adjustor 150 about the mating screw threads 143 and 155, causes o-ring 159 to be compressed against the distal face of bushing collar 27 thereby increasing the resistance to rotation of tubular frame 20. The set screw 158 may be tightened to secure the adjustor 150 in position when the desired resistance is obtained.

As seen in FIG. 1, the optional sheath 170 is seen to be a tubular member which slides over the tubular member 20. Mounted to the proximal end 172 of the sheath 170 is the convex hand grip member 175. Sheath 170 is concentrically and slideably mounted to the tubular frame 20. The inner diameter of sheath 170 is as close to the outer diameter of tubular frame 120 as conventional tolerances will allow in order to produce a minimum clearance which allows sliding of sheath 170 over tubular frame 20. In the at-rest position, sheath 170 is retracted to its maximum proximal position such that hand grip 175 is close to or touching knob 160 and the jaws 90 and 100 are exposed. In the actuated position, sheath 175 is slid axially and distally such that distal end 174 covers the jaws 90 and 100. This allows insertion of the ligating clip applier mechanism 10 through a conventional trocar while preventing the jaws 90 and 100 from damaging the trocar gasket conventionally contained in most trocars. The sheath 170 is retracted to the proximal at-rest position subsequent to insertion of the mechanism 10 through the trocar gasket, thereby exposing the jaws 90 and 100.

The elongate actuating member 80 is seen to be an elongate, cylindrical or tubular shaft-like member having spherical proximal end 82 and disk-like distal end 84. The member 80 has cylindrical bushing 88 concentrically mounted to serve as a spacer element within passage 25 of tubular member 20. The member 80 has spring collar slot 89 for mounting spring collar 65. Spring member 60 provides a proximal biasing force against link 56 of actuating trigger 50. The spring member 60 is concentrically mounted about the distal portion of member 80 between collar 65 and the face of proximal end 32 of ferrule 30. The elongate actuating member 80 is pivotally mounted at the proximal end 82 in mounting cavity 58 of link 56 which extends from trigger 50. The member 80 is slideably mounted within passage 25 of tubular frame 20. The proximal end of actuating member 80 distal to proximal end 82 is slideably mounted within passage 28 of bushing 26. The distal end 84 of actuating member 80 is mounted to the distal end 98 of jaw 90 in key hole slot 96. Counterclockwise rotation of actuating trigger 50 about pin 70 causes a distal displacement of elongate actuating member 80 along the longitudinal axis of tubular frame 20.

Such rotation also causes spring 65 to be compressed between collar 65 and the proximal end 32 of ferrule 30, thereby causing spring 65 to assert a proximal biasing force against collar 65.

Figure 5:
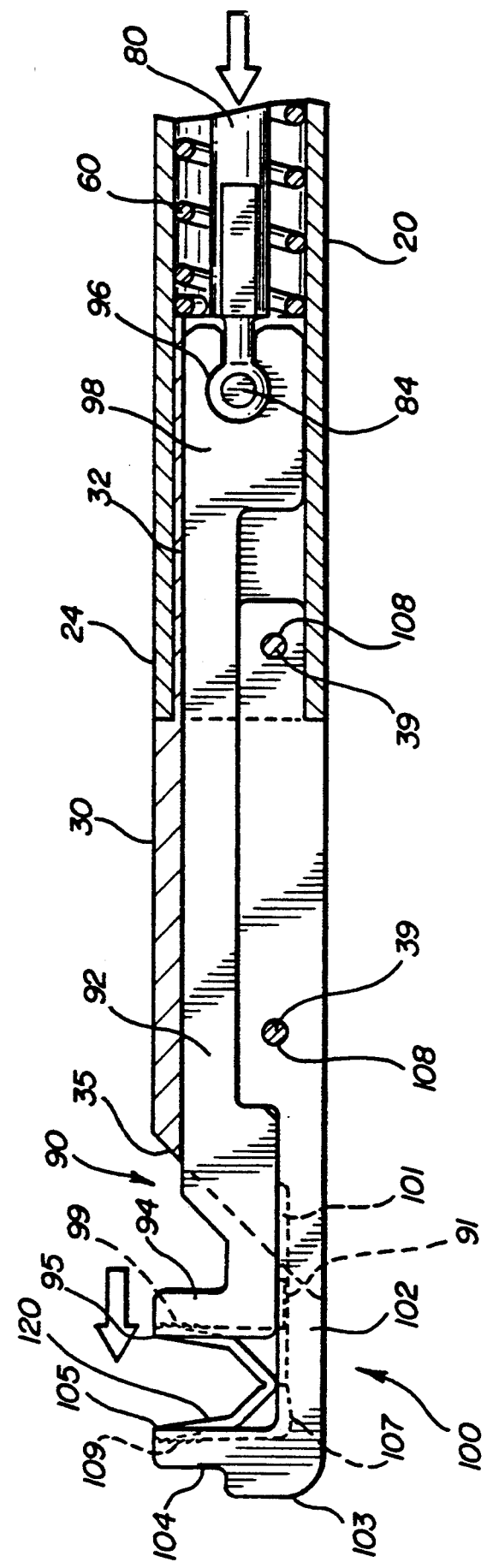
FIG. 5 is an enlarged partial cross-section of the distal end of the ligating clip applier mechanism of the present invention.

As can be seen in FIG. 3, FIG. 4, and FIG. 5, the stationary jaw 100 is mounted to the ferrule 30 and the distal end 24 of tubular frame 20 by pins 29 which are inserted through mounting holes 108 in member 102 and through mounting holes 28 in tubular frame 20 and mounting holes 37 in ferrule 30. The movable proximal jaw 90 is slidably mounted within the ferrule 30 and the distal end 24 of tube member 30. The moveable jaw 90 is mounted to the distal end 84 of elongate actuating member 80 so that when member 80 slides relative to tubular frame 20, the moveable jaw 90 also slides.

The stationary jaw 100 is seen to comprise an elongate member 102 having distal perpendicular leg 104 extending therefrom. The stationary jaw 100 has protuberance 103 extending distally from the distal end of elongate member 102 and the lower outer side of perpendicular leg 104. The perpendicular leg 104 of stationary jaw 100 has distal retention groove 105 containing optional teeth 109 for engaging clip 120. The stationary jaw 100 also contains curved rearward retention groove 107 in the top surface of member 102 proximal to leg 104. Longitudinal groove 101 contained in the upper surface of member 102 provides a track within which the lower tab member 91 of jaw 90 is slideably engaged.

The moveable jaw 90 is seen to be slideably mounted onto jaw member 102 within slot 37 of ferrule 30. The moveable jaw 90 is likewise seen to have elongate member 92 and distal perpendicular leg 94 extending upwardly therefrom. It can be seen that perpendicular leg 94 has proximal retention groove 95 containing optional teeth 99 for engaging clip 120. The proximal retention groove 95 and the distal retention groove 105 retain the legs 24 of a clip 120. Moveable jaw member 90 has tab member 91 which extends downwardly from the bottom of the distal end of elongate member 92 and which is engaged by, and slides within, groove 101 contained in elongate member 102. The proximal end 98 of elongate member 92 has keyhole slot 96 for engaging the distal, disk-like end 84 of actuating member 80. Typically the disk-like distal end 84 will be press fit into keyhole slot 96, but other conventional attachment methods such as welding may be used. It will be appreciated by those skilled in the art that in an alternate embodiment of the clip applier mechanism 10 of the present invention, the stationary jaw 100 may be made to be moveable while the jaw 90 is stationary. Alternately, both jaws 90 and 100 may be made to be slidable.

Figure 6:
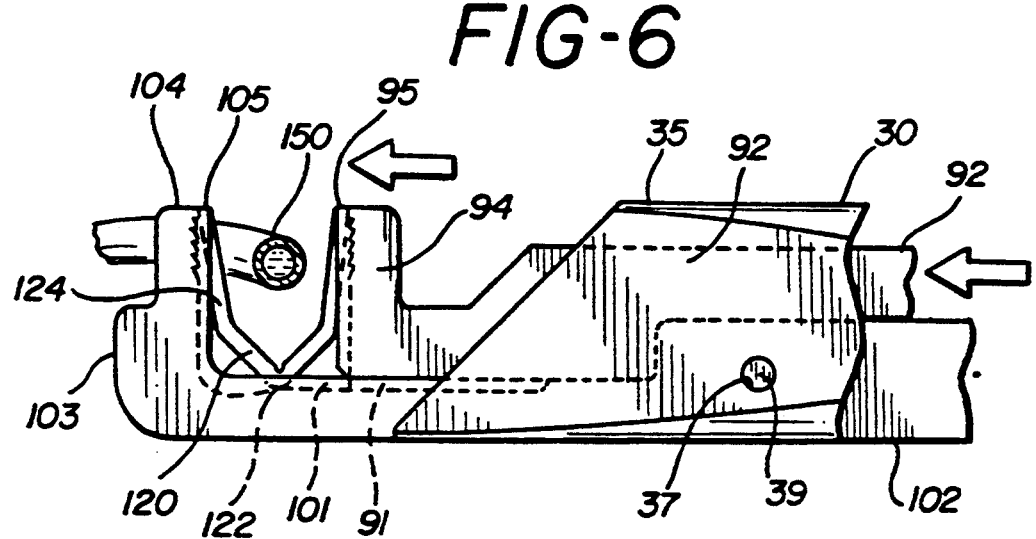
FIG. 6 is an enlarged side view of the jaws of the endoscopic clip applier mechanism of the present invention in the open position showing a clip and a blood vessel within the jaws.
Figure 7:
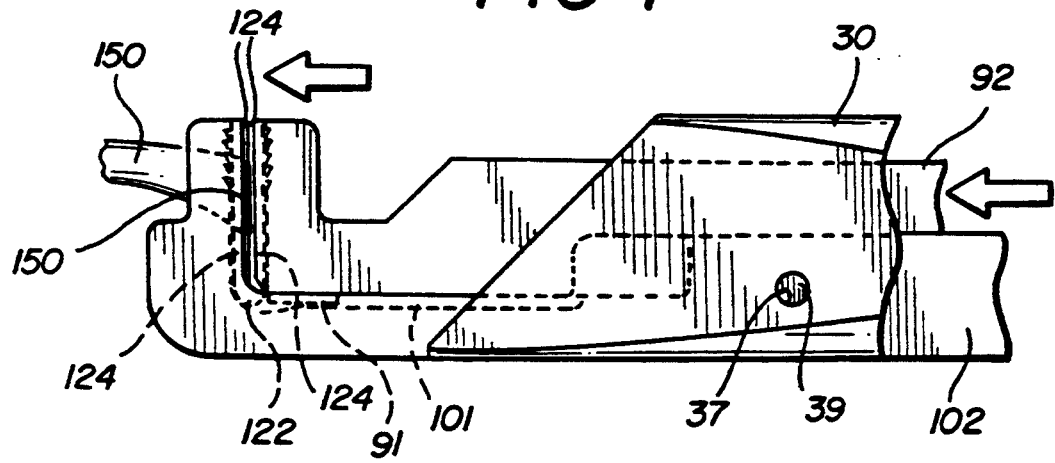
FIG. 7 is an enlarged side view of jaws of the present invention in the closed position illustrating a ligating clip which has been formed about a blood vessel.
Figure 8:
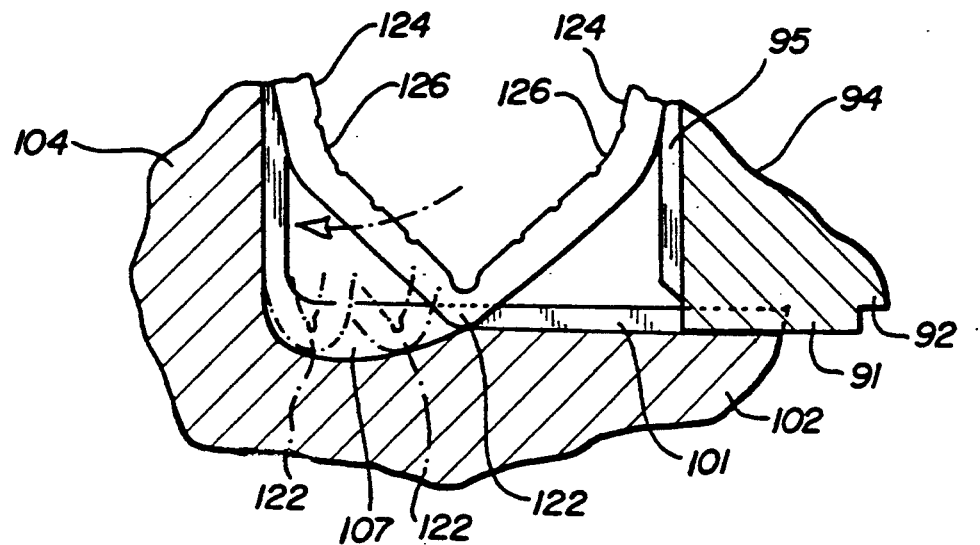
FIG. 8 is an enlarged partial cross section of the jaws of the present invention showing the movement of the apex of a ligating clip through a rearward retention groove in the stationary jaw as the clip is formed.

As can be seen in FIG. 6, FIG. 7, and FIG. 8, as the clip applier 10 is actuated and jaw 90 is displaced distally against clip 120, the apex 122 of the clip 120 is displaced both distally and downward into the rearward retention groove 107. It can be seen that positive reward retention of the clip 120 is produced throughout the closure of the jaws 90 and 100 since the apex 122 of the clip 120 is engaged by the distal retention curve 107 throughout formation of the clip 120.

The rearward retention groove 107 has sufficient depth and length to effectively provide positive rearward retention of apex 122 of clip 120 during formation. It will be appreciated that the length and depth of groove 107 will vary in accordance with the dimensions and mechanical characteristics of a particular clip 120. For example, when using a clip 120 having a height of 0.309" an outside width of 0.293" and a gauge thickness of 0.025" the length of groove 107 will typically be about 0.100" to about 0.150" more typically about 0.100" to about 0.115" and preferably about 0.104" to about 0.112". The depth of groove 107 will typically be about 0.010" to about 0.040" more typically about 0.020" to about 0.030" and preferably about 0.025" to about 0.027"

Referring to FIG. 2, the clip 120 is seen to have apex 122 and legs 124 extending angularly outward from the apex. The legs 124 are seen to have knees 126 located between the apex 122 and the distal ends 129 of the legs 124 at which point the legs are angulated inwardly such that the portions of legs 124 distal to the knees 126 are substantially parallel to the longitudinal axis of the clip 120. The longitudinal axis of the clip is defined to be the central axis extending from the apex outward between the legs 124. When a clip 120 is loaded into the jaws 100 and 90, the legs 124 are retained in the grooves 95 and 105 from the knees 126 to the distal ends 129. The portions of the legs 124 proximal to the knees 126 and distal to the apex 122, along with the apex 120, are typically not contained by the grooves 95 and 105. The outer surfaces of the legs 124 are seen to have optional teeth 129 for mating with optional teeth 109 and 99 in retention grooves 95 and 105.

Referring to FIG. 1, a clip cartridge 110 is seen to contain a plurality of clips 120 in slots 111. Each clip 120 has an apex 122, legs 124, knees 126 and distal ends 129.

Although not shown in the drawings, the jaws 90 and 100 may have optional coining means 180 mounted therein. Coining means 180 may consist of at least one shaped member 185 extending longitudinally from at least one of the jaw legs 104 or 94. A shaped member 185 may be positioned to apply a coining force to the apex 122 when the clip 120 is formed in order to reduce the gap in the apex 122, and may be positioned in an effective manner to apply coining forces to other parts of the clip gap such as the knee gap.

Figure 9:
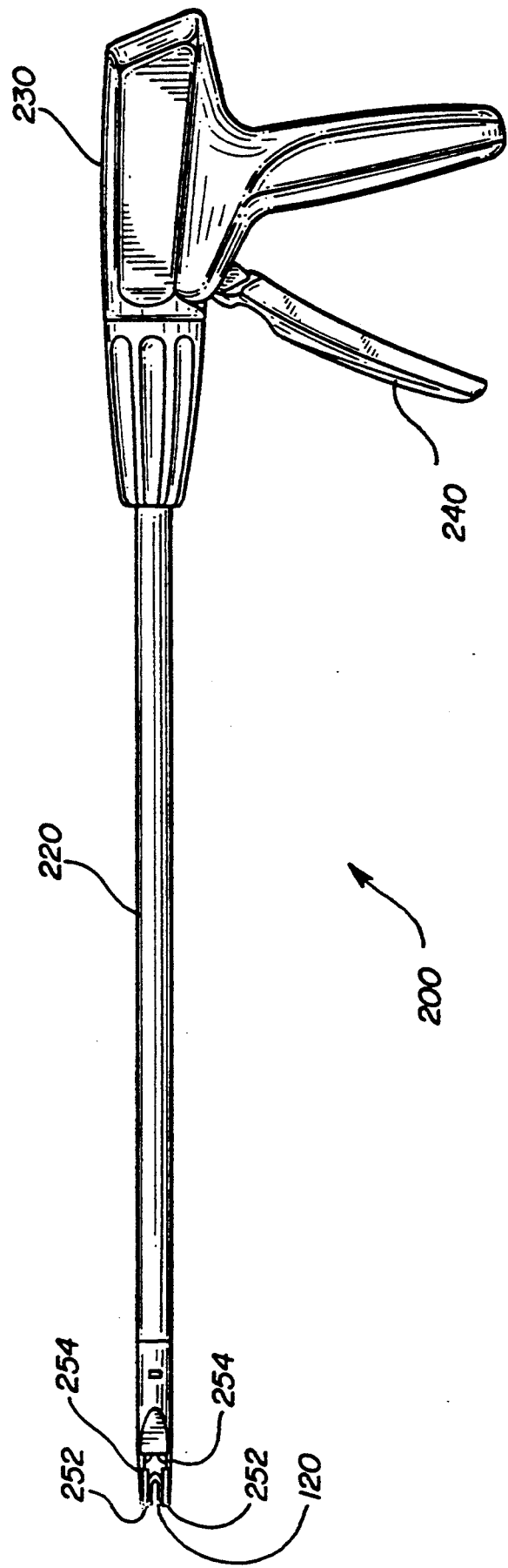
FIG. 9 is a side elevational view of an endoscopic ligating clip of applier of the prior art.
Figure 10:
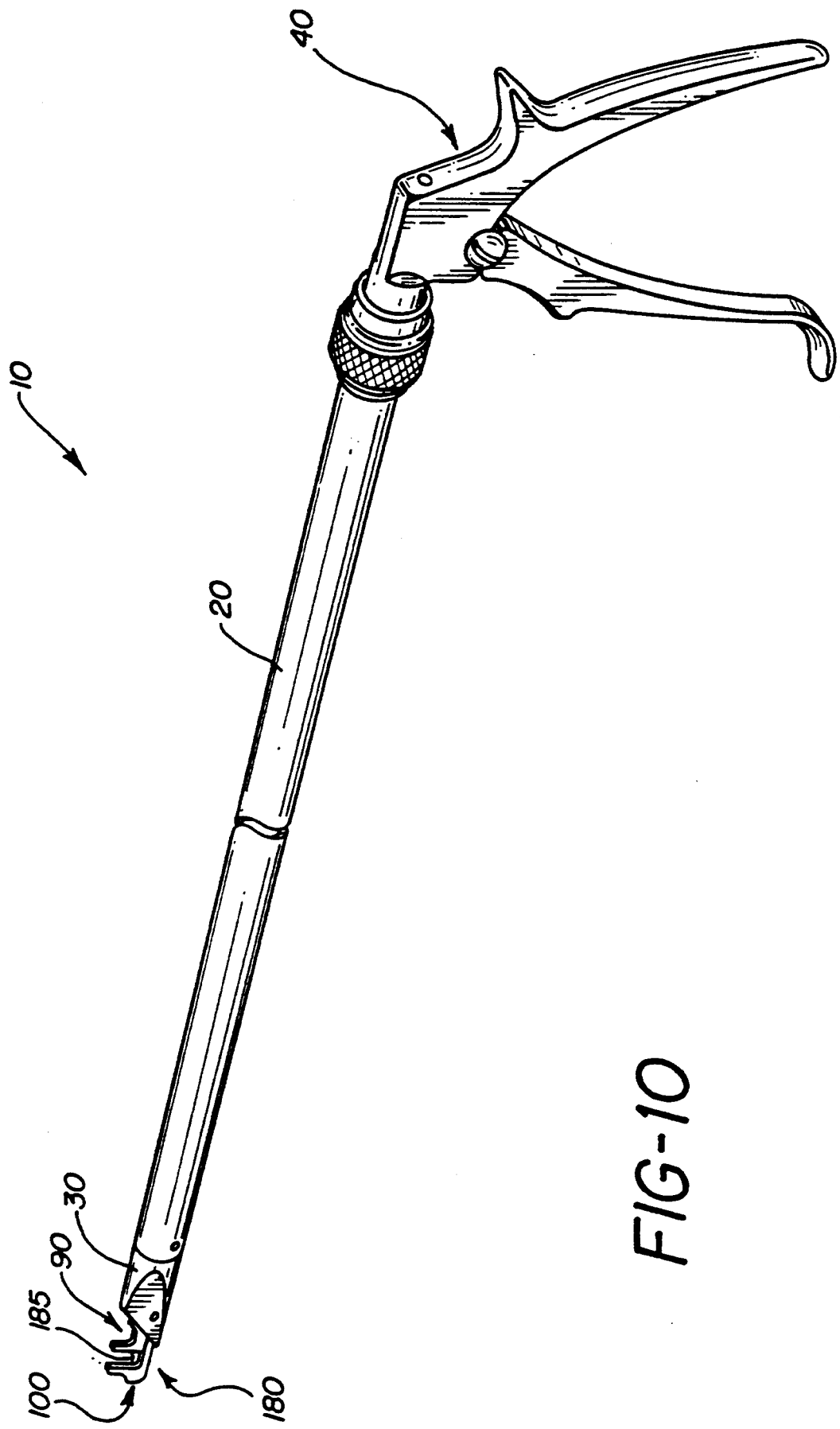
FIG. 10 is a partial perspective view of a clip applier of the present invention having a coining means extending from one jaw.
Figure 11:
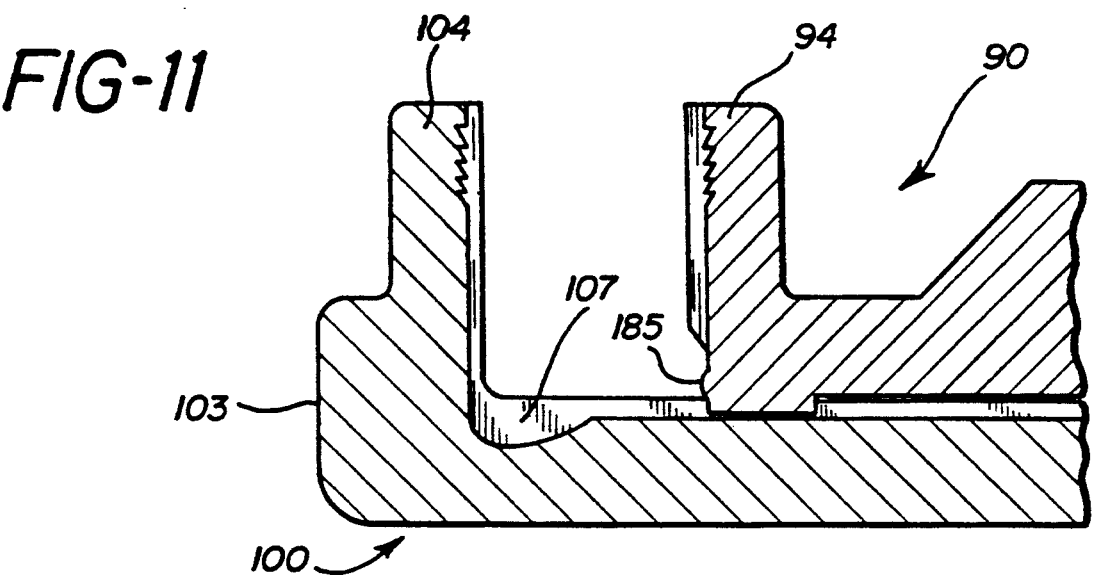
FIG. 11 is a partial cutaway view of the jaws of the clip applier of FIG. 10 having a shaped member extending distally from the bottom of the proximal jaw.
Figure 12:
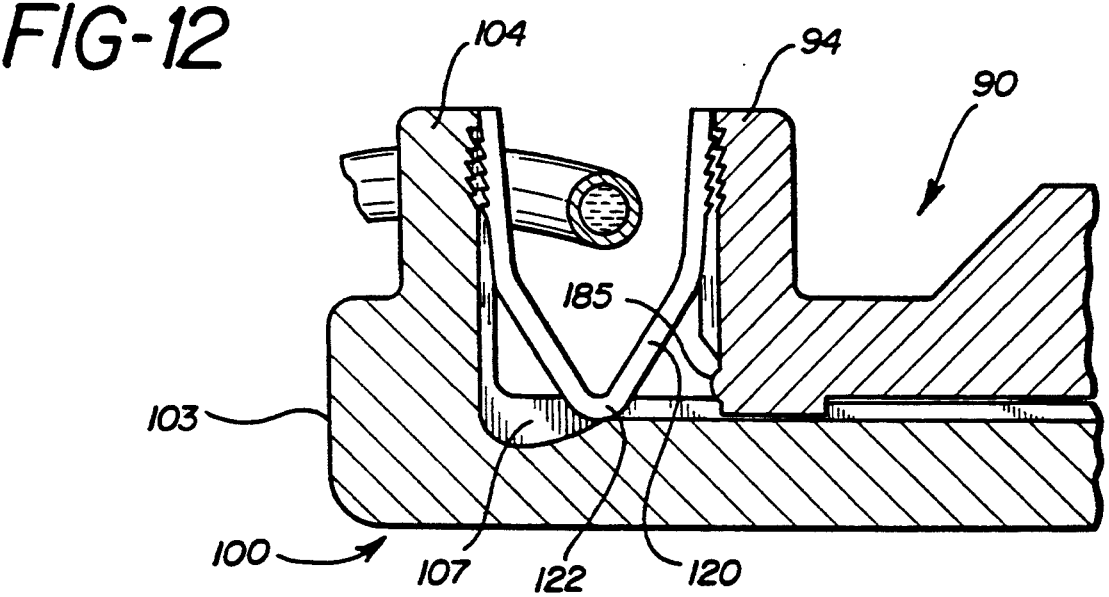
FIG. 12 illustrates a ligating clip contained within the jaws of FIG. 11 with a blood vessel positioned within the clip prior to formation.
Figure 13:
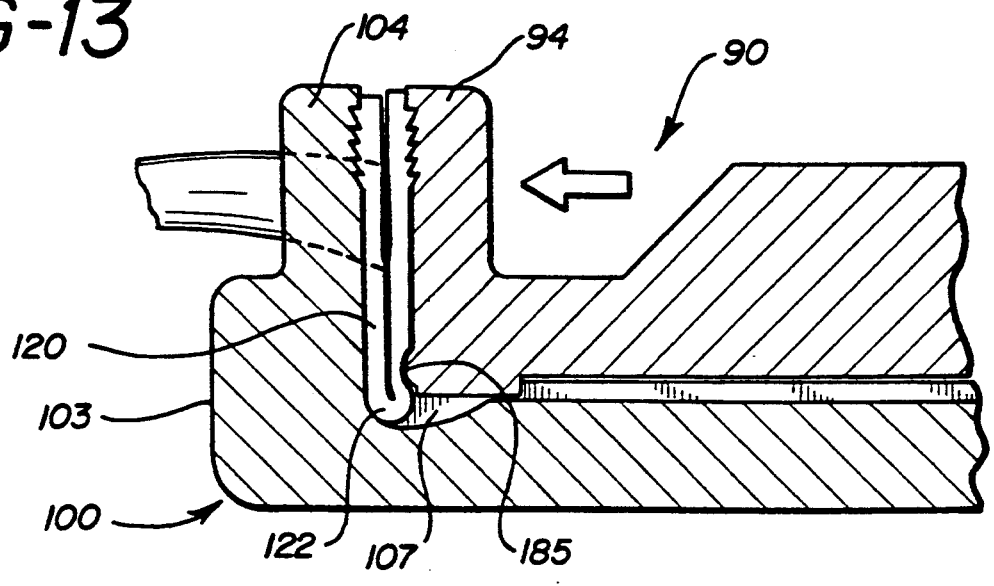
FIG. 13 illustrates the clip of FIG. 12 formed about the blood vessel showing the shaped member coining the apex of the clip.

Referring to FIG. 9, a conventional ligating clip applier apparatus 200 is illustrated. The clip applier apparatus 200 has elongate tubular frame 220 to which handle 230 is attached. The clip applier 200 has actuating trigger 240, conventional actuating means 260 (not shown) and distal jaws 250 having retention grooves 252. The jaws 250 are seen to be slightly angulated with respect to each other and have outer cam surfaces 254. Actuation of the trigger 240 causes actuating means 260, typically a cam channel, to move distally to engage the cam surfaces and force the jaws 250 inwardly. It can be seen in FIG. 9 that a ligating clip 120 is contained within the jaws 250. It can be appreciated by those skilled in the art that the degrees of freedom for manipulation of tissue are limited with this type of ligating clip applier. Specifically, it can be appreciated that the ligating clip applier apparatus 200 may be used to move blood vessels or tissue up or down, left or right, and in. In contrast, the ligating clip applier mechanism 10 of the present invention, having jaws 90 and 100, which are mounted substantially perpendicular to the longitudinal axis of the mechanism 10, allows a surgeon to move tissue or blood vessels in and out, as well as up and down and left and right, thereby providing three full degrees of freedom. In addition, it can be seen that the clip 120 in the ligating clip applier 200 is free to move rearward within the jaws 250. Typically, a clip 120 moves proximally in the clip retention grooves as the clip is formed by the jaws 250. If appropriate adjustments are not made by the the surgeon, this unrestrained proximal movement may result, for example, in the clip not being formed completely about all of the tissue that was intended, since the clip is displaced proximally with respect to the stationary tissue. In addition, since the apex 122 is not restrained or contained rearwardly, and further due to the angulation of the jaws 250 with respect to each other, it is extremely difficult, if not impossible, to minimize the clip gap, including the gap at the apex 122 of the clip 120, when the clip 120 is formed.

Clip gap is defined to mean the gaps in a formed clip 120 between the inner surfaces of the legs 124. Typically an apex gap is present in the formed clip as are one or more gaps distal to the apex gap, e.g., the knee gap. It is particularly difficult to minimize the apex gap using conventional ligating clip appliers. The clip gap of clips formed using conventional ligating clip appliers is typically in the range of about 0.0035 inches to about 0.0075 inches. In contrast the clip gap of a formed clip 120 using the ligating clip applier mechanism 10 the present invention is substantially reduced and is typically in the range of less than about 0.0005 inches to about 0.003 inches, more typically less than about 0.0005 inches to about 0.002 inches and preferably less than about 0.0005 inches to about 0.001 inches.

Endoscopic surgical techniques are widely known, e.g., *Textbook of Laparoscopy*, J.F. Hulka, M.D., Gruse & Stratton, Inc., New York (1985) which is incorporated by reference. Typically, a patient is initially anesthetized using conventional anesthesia and techniques. Then a body cavity of the patient containing the target surgical site is insufflated with a gas such as carbon dioxide. Next, the surgeon inserts several conventional trocars into the body cavity, removing the obturators and leaving trocar cannulas as pathways to the body cavity. The trocar cannulas are used to insert various endoscopic instruments into the body cavity such as ligating clip appliers, staplers, endoscopes, sutures and the like.

When using the ligating clip applier mechanism 10 of the present invention in an endoscopic surgical procedure, initially a clip 120 is loaded between jaw 100 and jaw 90 by inserting perpendicular legs 104 and 94 into a slot 111 in cartridge 110 containing a clip 120. A clip 120 is then engaged in the grooves 95 and 105 of the legs 94 and 104. Then the legs 104 and 94 and clip 120 are removed from the slot 111 in cartridge 110. Next, the ligating clip applier mechanism 10 is inserted through a conventional trocar cannula into a body cavity of a mammal, for example, the abdominal cavity. When using the mechanism 10 with the optional sheath 170, the sheath 170 is slid distally so that distal end 174 covers the jaws 90 and 100 prior to insertion through the conventional entrance gasket of the trocar cannula. Then, after insertion, the sheath 170 is retracted proximally to expose the jaws 90 and 100. As can be seen in FIG. 6, when in the abdominal cavity of the mammal, the surgeon locates and places the jaws 90 and 100 containing the clip 120 about tissue or a blood vessel 150. The surgeon may then maneuver, e.g., the blood vessel 150, in and out, up and down, or left and right (i.e., three degrees of freedom). When the blood vessel 150 is properly positioned between the jaws 100 and 90, the surgeon then actuates the actuating trigger 50 by rotating the trigger in a counterclockwise direction about the pivot pin 70.

This causes the elongate actuating member 80 to displace in a distal direction, along with jaw 90, thereby causing the clip 120 to be formed about the blood vessel 150 as jaw 90 is displaced distally toward stationary jaw 100. As the clip 120 is being formed, the apex 122 of the clip 120 is contained within positive rearward retention groove 107. When the blood vessel 150 has been fully ligated, the surgeon releases the trigger 50 and the proximal bias provided by the compressed spring member 60, acting against collar 65 of elongate actuating member 80, which in turn acts upon link 56, causes the trigger 50 to rotate about pin 70 in a clockwise rotation to a resting position, thereby causing elongate actuating member 80 to be displaced in a proximal direction and likewise displacing slidable jaw member 90 in a proximal direction to a resting position. The surgeon typically applies a plurality of clips to the tissue or blood vessel, e.g., two or three on either side of an intended cut. The surgeon then maneuvers the mechanism 10 such that the ligated blood vessel is displaced out from between the jaws members 100 and 90, and then removes the mechanism 10 from the body cavity through the trocar cannula. As can be seen in FIG. 8, the apex 122 of the clip 120 moves into and is contained by distal retention curve groove 107 as the jaw member 90 is displaced distally, thereby forming the clip 120. It has not been previously possible to form a ligating clip 120 while having positive rearward retention of the apex of the clip throughout the clip closure and without sliding the clip 120 in relation to the jaw grooves.

The ligating clip applier mechanism 10 of the present invention has many advantages. First of all, the ligating clip applier mechanism 10 is, surprisingly, easily inserted through a 10 mm trocar cannula, even though the jaws 90 and 100 are substantially perpendicular to the longitudinal axis of the mechanism 10. An additional advantage is that the ligating clip applier mechanism 10 provides the surgeon with 3 degrees of freedom when manipulating tissue or blood vessels within the body cavity of a patient. The ligating clip applier mechanism 10 may be used to manipulate tissue either with or without a ligating clip 20 contained in the jaws 90 and 100.

Another advantage of the ligating clip applier mechanism 10 of the present invention is that it is now possible to apply ligating clips 120 while having positive rearward retention of the clip 120. This allows the apex 122 of the clip 120 to be formed such that the clip gap (including apex gap and knee gap) between the legs 124 of the clip 120 is substantially reduced when compared with conventional clips 120 formed using ligating clip appliers. The positive rearward retention feature reduces the incidence of misapplication of a formed clip about blood vessels or tissue.

Yet another advantage of the ligating clip applier mechanism 10 of the present invention is that a blood vessel or tissue is more readily observable within the jaws 90 and 100 of the mechanism 10 as compared with the jaws of a conventional ligating clip applier 200. Conventional endoscopic viewing apparatuses do not provide the surgeon with depth of field. Consequently, it is difficult for the physician to be absolutely certain that the blood vessel or tissue is within the jaws of a conventional clip applier prior to forming the clip. The surgeon must use judgment based upon experience. Using the mechanism 10 of the present invention, the physician can readily see the position of tissue or blood vessel in front of the perpendicular leg 104 of stationary jaw 100 and be substantially assured that the tissue is properly positioned for forming.

A further advantage of the mechanism 10 of the present invention is that it is now possible to incorporate coining means into the jaws of the mechanism thereby allowing the clip gap to be reduced, for example, the apex of a ligating clip can be coined in order to reduce the apex gap. The knee gap or other gaps can be similarly reduced by coining.

Yet another advantage of the clip applier mechanism 10 of the present invention is that, for the first time, it is now possible to insert an open ligating clip in the jaws of a ligating clip applier wherein the maximum outside width of the clip is equal to or greater then the interior diameter of the trocar. It can be appreciate that the maximum width of a clip 120 that can be inserted into a conventional trocar is by necessity less than the interior diameter of a trocar since the width of the clip 120 must be contained within the jaws of the conventional clip applier. Width of a clip 120 means the maximum distance between the outside of the legs 124 of the clip 120. Since the jaws of a conventional clip applier are somewhat aligned with the longitudinal axis of the clip applier and the clip applier jaws straddle the outside of the legs of a clip 120, the maximum width of a clip 120 that will fit through a particular trocar cannula is equal to the inner diameter of the torcar cannula, minus the thickness of each jaw. When using the clip applier mechanism 10 of the present invention, however, it is possible to have a clip with a width equal to or greater than the internal diameter of the particular trocar since the width dimension of the clip will be parallel to the longitudinal axis of the trocar. For example, typically the maximum width of a clip 120 that is used to fit through a conventional 10 mm trocar using a conventional clip applier is about 0.167". However, when using the clip applier mechanism 10 of the present invention, it easy to use clips 120 having a maximum width in excess of 0.250". The width of a conventional 10 mm trocar is 0.393".

It will be appreciated by those skilled in the art that the clip applier mechanism 10 of the present invention may be used in conventional, open surgical techniques in a similar manner to ligate and manipulate tissue and blood vessels. Similar advantages will be present when used with conventional surgical techniques.

Of course, it can be conceived that this mechanism can easily be converted into a repeatable, multiple fire clip applying mechanism. For instance, contained in frame 20 there may be loaded a stack of clips 120, each having their legs placed side-to-side. In this way, the clips 120 may be spring biased, in order to proceed toward the jaws 90, 100 of the current mechanism. The distal most clip 120 may be spring loaded from a transfer station immediately behind jaws 90, 100 to a position between the jaws, using conventional transfer means, similar as those described in U.S. patent application No. 779,420, assigned to a common assignee as the present invention, and incorporated herein by reference. Thus, a multiple applier mechanism of this sort allows for continual application at the surgical situs, without the reloading requirements of a single-fire device.

Although this invention has been shown and described with respect to detailed embodiments thereof, it will be understood by those skilled in the art that various changes in form and detail thereof may be made without departing from the spirit and scope of the claimed invention.

What is claimed is:

1. An endoscopic clip applier for forming ligating clips wherein the clips have an apex, the clip applier comprising:
    an actuating mechanism;
    an elongated shaft connected to said actuating mechanism and defining a longitudinal axis; and
    a pair of jaws connected to said elongated shaft,
    said jaws remotely actuated by said actuating mechanism, and said jaws maintained at substantially perpendicular angles to said longitudinal axis, wherein the jaws comprise at least one rearward retention groove having a longitudinal axis, the groove sufficiently long and deep to effectively retain the apex of a ligating clip during at least part of the forming process, wherein the longitudinal axis of said rearward retention groove is substantially parallel to said longitudinal axis.

2. The clip applier of claim 1 wherein said jaws are capable of sliding one with respect to the other along said longitudinal axis.

3. The clip applier of claim 1 wherein one of said jaws is stationary.

4. The clip applier of claim 1 wherein the distal most of said jaws is stationary.

5. The clip applier of claim 1 wherein the actuating mechanism comprises a pair of handles.

6. The clip applier of claim 1 wherein said shaft is rotatable about the longitudinal axis.

7. The clip applier of claim 1 wherein said jaws contain a coining means.

8. The clip applier of claim 1 additionally comprising a ligating clip wherein said clip is applied around a blood vessel to achieve a closure of less than about 0.003".

9. The clip applier of claim 1 additionally comprising a stack of ligating clips wherein the stack of clips is loaded within said shaft.

10. The clip applier of claim 9 wherein a clip may be loaded from said stack to a position between said jaws by means of a clip transfer mechanism located at the distal end of said stack.

11. An endoscopic clip applier for forming ligating clips wherein the clips have an apex, the clip applier comprising:
    an elongated shaft defining a longitudinal axis;
    a pair of clip applying jaws connected to said shaft, said jaws identified as a proximal jaw and a distal jaw said jaws maintained at substantially perpendicular angles to said longitudinal axis wherein said distal jaw is capable of engaging tissue such that said tissue may be held between said jaws and transversely to said shaft wherein the jaws comprise at least one rearward retention groove having a longitudinal axis, the groove sufficiently long and deep to effectively retain the apex of a ligating clip during at least part of the forming process wherein the longitudinal axis of said rearward retention groove is substantially parallel to said longitudinal axis; an actuating mechanism for operating said jaws.

12. The clip applier of claim 11 wherein said jaws are capable of sliding one with respect to the other along said longitudinal axis.

13. The clip applier of claim 11 wherein one of said jaws is stationary.

14. The clip applier of claim 11 wherein the distal most of said jaws is stationary.

15. The clip applier of claim 11 wherein the actuating mechanism comprises a pair of handles.

16. The clip applier of claim 11 wherein said shaft is rotatable about the longitudinal axis.

17. The clip applier of claim 11 wherein said jaws contain a coining means.

18. The clip applier of claim 12 wherein said clip is applied around a blood vessel or tissue to achieve a closure of less than about 0.003".

19. The clip applier of claim 11 where a stack of clips is loaded within said shaft.

20. The clip applier of claim 19 wherein a clip may be loaded from said stack to a position between said jaws by means of a clip transfer mechanism located at the distal end of said stack.

21. An endoscopic clip applier for forming ligating clips wherein the clips have an apex, the clip applier comprising:
a pair of clip applying jaws, one of said jaws stationary with respect to said mechanism, and the second of said jaws slidable with respect to said mechanism;
an elongate shaft defining a longitudinal axis parallel to the length of said shaft; and,
an actuating mechanism attached to said shaft for operating said jaws, wherein said jaws are substantially perpendicular to the longitudinal axis and wherein the jaws comprise at least one rearward retention groove having a longitudinal axis, the groove sufficiently long and deep to effectively retain the apex of a ligating clip during at least part of the forming process and wherein longitudinal axis of said rearward retention groove is substantially parallel to said.

22. The clip applier of claim 21 wherein said jaws are capable of sliding one with respect to the other along said longitudinal axis.

23. The clip applier of claim 21 wherein one of said jaws is stationary.

24. The clip applier of claim 21 wherein the distal most of said jaws is stationary.

25. The clip applier of claim 21 wherein the actuating mechanism comprises a pair of handles.

26. The clip applier of claim 21 wherein said shaft is rotatable about the longitudinal axis.

27. The clip applier of claim 21 wherein said jaws contain a coining means.

28. The clip applier of claim 21 wherein said clip is applied around a blood vessel or tissue to achieve a closure of less than about 0.003".

29. The clip applier of claim 21 where a stack of clips is loaded within said shaft.

30. The clip applier of claim 21 wherein a clip may be loaded from said stack to a position between said jaws by means of a clip transfer mechanism located at the distal end of said stack.

31. A method of forming a ligating clip, wherein the ligating clip has an apex, comprising
a) inserting a ligating clip into the jaws of a ligating clip applier, wherein the clip applier comprises:
an actuating mechanism;
an elongated shaft connected to said actuating mechanism and defining a longitudinal axis; and
a pair of jaws connected to said elongated shaft,
said jaws remotely actuated by said actuating mechanism, and
said jaws maintained at substantially perpendicular angels to said longitudinal axis and wherein the jaws comprise at least one rearward retention groove having a longitudinal axis, the groove sufficiently long and deep to effectively retain the apex of a ligating clip during at least part of the forming process and wherein the longitudinal axis of said rearward retention groove is substantially parallel to said longitudinal axis; and,
b) actuating the mechanism to form the clip.

32. A method of performing an endoscopic surgical procedure, comprising
a) using an endoscopic ligating clip applier, wherein the clip applier comprises:
an actuating mechanism;
an elongated shaft connected to said actuating mechanism and defining a longitudinal axis; and
a pair of jaws connected to said elongated shaft,
said jaws remotely actuated by said actuating mechanism, and
said jaws maintained at substantially perpendicular angels to said longitudinal axis and wherein said jaws comprise at least one rearward retention groove having a longitudinal axis, the groove sufficiently long and deep to effectively retain the apex of ligating clip during at least part of a forming process wherein the longitudinal axis of said rearward retention groove is substantially parallel to the longitudinal axis;
b) inserting an open ligating clip into the jaws wherein the clip has an apex.

33. The method of claim 32 wherein the clip is inserted into the jaws prior to insertion into the body cavity.

34. The method of claim 32 wherein the clip is inserted into the jaws after insertion of the mechanism into the body cavity.

35. The method of claim 32 wherein the mechanism is inserted into the body cavity through a trocar.

36. A method of performing a surgical procedure, comprising
a) using a ligating clip applier wherein the clip applier comprises:
an actuating mechanism;
an elongated shaft connected to said actuating mechanism and defining longitudinal axis; and
a pair of jaws connected to said elongated shaft,
and jaws remotely actuated by said actuating mechanism, and
said jaws maintained at substantially perpendicular angles to said longitudinal axis wherein said jaws comprise at least one rearward retention groove sufficiently long and deep to effectively retain the apex of a ligating clip during the forming process wherein the longitudinal axis of said rearward retention groove is substantially parallel to the longitudinal axis;
b) inserting an open ligating clip into the jaws;
c) positioning a blood vessel or tissue within the jaws of the mechanism; and,
d) actuating the actuating mechanism to form a clip about the blood vessel or tissue.

37. The method of claim 36 wherein the clip is inserted into the jaws prior to insertion into the body cavity.

38. The method of claim 36 wherein the clip is inserted into the jaws after insertion of the mechanism into the body cavity.

* * * * *